US00PP11251P

United States Patent [19]

Zary

[11] Patent Number: Plant 11,251

[45] Date of Patent: Feb. 29, 2000

[54] SHRUB ROSE PLANT NAMED 'JACPURSH'

[75] Inventor: Keith W. Zary, Thousand Oaks, Calif.

[73] Assignee: Bear Creek Gardens, Inc., Medford, Oreg.

[21] Appl. No.: 09/000,607

[22] Filed: Dec. 30, 1997

[51] Int. Cl.[7] ..... A01H 5/00

[52] U.S. Cl. ..... Plt./108

[58] Field of Search ..... Plt./102, 107, 108, Plt./149, 150

*Primary Examiner*—Howard J. Locker

*Attorney, Agent, or Firm*—Klarquist Sparkman Campbell Leigh & Whinston, LLP

[57] ABSTRACT

Shrub rose plant with dark green, glossy foliage; vigorous, upright growth habit; fragrant flower with rapid petal drop; ability to root and grow from hardwood cuttings; resistance to disease; and production of bright orange hips.

1 Drawing Sheet

The present invention relates to a new and distinct variety of rose plant of the schrub class which was originated by me by crossing an unnamed seedling with the variety 'JACsedi' (U.S. Plant Pat. No. 9,172).

The primary objective of this breeding was to produce a new rose variety having the excellent hardwood cutting rooting ability, the clean petal drop, and vigorous well-branched growth habit of the unnamed lavender shrub female parent combined with the very glossy foliage, purple flowers, and fragrance of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright well-branched growth habit;
2. Fragrant flowers;
3. Excellent ability to root from hardwood cuttings;
4. Glossy, disease resistant foliage;
5. Ability to drop petals cleanly;
6. Production of bright orange hips.

'JACpursh' also produces green fruit turning in August and September to orange. These fruit are substantially spherical (¾" in diameter) and contain up to twenty seeds. Production of fruit does not prevent continued flowering. Fruit is persistant until late November in Somis, Calif., when it drops.

Asexual reproduction of this new variety by hardwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—'JACsedi' (U.S. Plant Pat. No. 9,172).

Classification:

*Botanical.*—*Rosa hybrida.*

*Commercial.*—Shrub.

FLOWER

Observations made from specimens grown in a garden environment at Somis, Calif. from January 1996–August 1997.

Blooming habit: Continuous.

Bud:

*Size.*—One and one-quarter inches long when the petals start to unfurl.

*Form.*—The bud form is long, pointed ovoid.

*Color.*—When sepals first divide, bud color is close to Red Group 53B with some streaks of Red Group 53C. When half blown, the upper sides of the petals are Red Group 53B with some white streaks and some fading toward petal edges to Red Group 53C; and the lower sides of the petals are Red Group 53B.

*Sepals.*—Color: Green group 138B with a distinct bronze color in the older sepals. Surface texture: Covered with fine hairs. There are three lightly appendaged sepals. There are two unappendaged sepals with hairy edges.

*Receptacle.*—Color: Green Group 137D. Shape: Funnel. Size: Small (¼"×3/16"). Surface: Smooth.

*Peduncle.*—Length: Short (2½"–3"). Surface: Smooth. Color: Light green becoming increasingly bronzy as it ages. Strength: Stiff, erect.

Bloom:

*Size.*—Small. Average open size is 2½–3 inches.

*Borne.*—Several together in rounded clusters of five to nine flowers.

*Stems.*—Medium (14"–18"), strong.

*Form.*—When first open: High centered. Permanence: Flattens.

*Petalage.*—Number of petals under normal conditions: 15–20.

*Color.*—The upper sides of the petals are Red Group 53B with some white streaks and some fading on petal edges to Red Group 53C. The reverse sides of the petals are Red Group 53C. The base of each petal has a distinctive "white eye" which is a change in color from Red Group 53B to White Group 155D. There is also a small (⅛"×⅛"), Yellow Group 4C half moon at the point of attachment. The major color on the upper side is Red Group 53B.

*Variegations.*—There are occasional white streaks on some petals.

*Discoloration.*—At the end of the first day: No change. At the end of the third day: No change. By day four or five, depending on temperature and sunlight intensity, there is a fading to Red Group 53C, then Red Group 53D. Petal drop is on day six or seven.

*Fragrance.*—Moderate.

Petals:

*Texture.*—Thick.

*Shape.*—Deltoid.

*Form.*—Tips slightly recurved.

*Arrangement.*—Imbricated. Petaloids in the center are few.

*Persistence.*—Drop off cleanly.

*Lastingness.*—On the plant: Fair (six or seven days). As a cut flower: Not tested.

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Reddish-brown.

*Stigmas.*—Color: Greenish-white.

Plant:

*Form.*—Shrub.

*Growth.*—Vigorous; upright; branching; Height after one year of growth on its own roots in Somis, Calif. is four and one-half to five feet while the width is three to three and one-half feet.

Foliage: Number of leaflets on normal mid-stem leaves: Five or seven.

*Size.*—Large (7 to 8"×4 to 5").

*Quantity.*—Abundant.

*Color.*—New foliage: Upper and lower surfaces: Greyed-Red Group 178A. Old foliage: Upper surface: Green Group 139A. Lower surface: Green Group 138C.

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth with occasional prickles.

*Stipules.*—Medium (½" to ⅝"); serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary to few (⅜" to ½"). On laterals from main canes: Ordinary to few (¼").

*Form.*—Medium; hooked slightly downward.

*Color when young.*—Red.

Small prickles:

*Quantity.*—On main stalks: None. On laterals: None.

I claim:

1. A new and distinct variety of rose plant of the shrub class, substantially as herein shown and described, characterized particularly as to novelty by dark green, glossy foliage; vigorous, upright growth habit; fragrant flower; ability to root and grow from hardwood cuttings; resistance to disease; rapid petal drop; and production of bright orange hips.

* * * * *

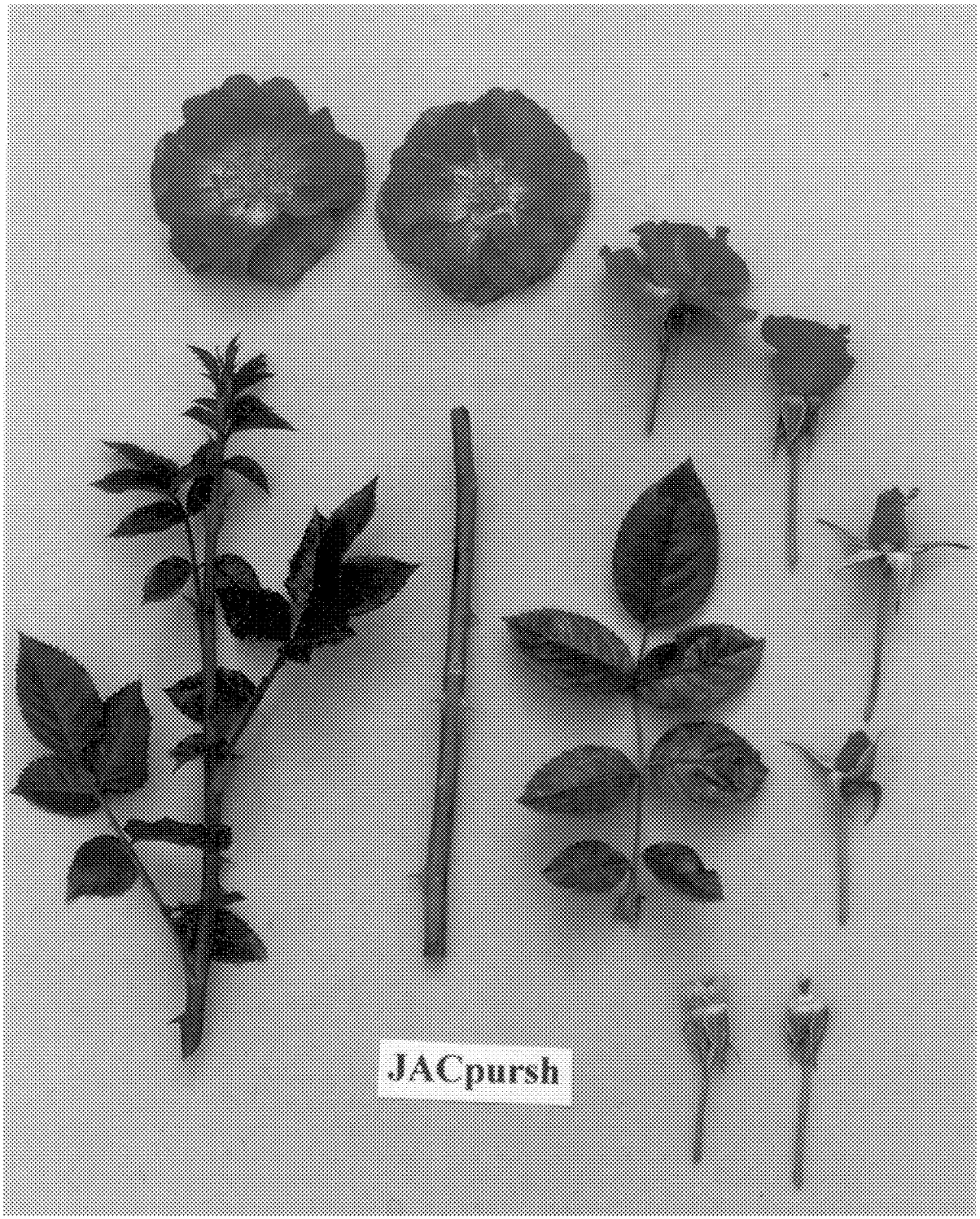
JACpursh